United States Patent [19]
Deckers

[11] Patent Number: 5,406,240
[45] Date of Patent: Apr. 11, 1995

[54] DEVICE TO REDUCE THE HAZARDS OF SURROUNDING ELECTROMAGNETIC RADIATION

[76] Inventor: Francois E. Deckers, Batticelaan 22, 1932 Sint-Stevens-Woluwe, Belgium

[21] Appl. No.: 150,483

[22] Filed: Nov. 12, 1993

Related U.S. Application Data

[63] Continuation-in-part of Ser. No. 725,042, Jul. 3, 1991, abandoned, which is a continuation-in-part of Ser. No. 70,946, Jul. 8, 1987, abandoned.

[30] Foreign Application Priority Data

Jun. 5, 1987 [BE] Belgium ................. 87-00622

[51] Int. Cl.⁶ ............ H01H 1/00; H01H 5/00
[52] U.S. Cl. ..................... 335/214; 315/8; 335/302; 335/306
[58] Field of Search ......... 313/440; 315/8, 35; 174/32-35 TS; 335/211, 212, 214, 302-306

[56] References Cited

U.S. PATENT DOCUMENTS

| | | | |
|---|---|---|---|
| 2,894,235 | 7/1959 | Stamberger | 338/52 |
| 3,110,516 | 11/1963 | Sukala | 335/303 |
| 3,230,294 | 1/1966 | McAdams | 174/35 |
| 3,260,788 | 1/1966 | Stetson | 174/35 |
| 3,508,219 | 4/1970 | Brownlow et al. | 335/303 |
| 3,546,643 | 12/1970 | Virostek | 335/303 |
| 3,615,993 | 10/1971 | French | 156/155 |
| 3,889,043 | 6/1975 | Ducros | 174/35 |
| 4,218,507 | 8/1980 | Deffeyes et al. | 428/328 |
| 4,253,078 | 2/1981 | Tagawa et al. | 335/212 |
| 4,392,083 | 7/1983 | Costello | 315/85 |
| 4,695,694 | 9/1987 | Hill et al. | 219/10.55 D |
| 4,709,220 | 11/1987 | Sakane et al. | 335/214 |
| 4,733,455 | 3/1988 | Nakamura et al. | 29/603 |

FOREIGN PATENT DOCUMENTS 2159822 12/1985 United Kingdom .

OTHER PUBLICATIONS

"Conditions of Work Digest", International Labour Office, Geneva, vol. 5, No. 1, (1986) p. 59, 146–147, 172–173.

"All Eyes on the VDT—Is working at a computer terminal hazardous to your health?", *Time*, (Jun. 27, 1988), p. 51.

*Primary Examiner*—Leo P. Picard
*Assistant Examiner*—Raymond M. Barrera
*Attorney, Agent, or Firm*—Kramer, Brufsky & Cifelli

[57] ABSTRACT

In combination with an electric apparatus emitting electromagnetic radiation, an arrangement for reducing the radiation hazards on an operator in front of the apparatus is provided, the arrangement comprising at least three magnetic devices approximately located at the apices of a triangle in front of the apparatus, each magnetic device including a closed housing made of a non-magnetic material, a permanetn magnet located within the housing for producing a magnetic flux, and a bar of non-magnetic material located within the housing in a defined spaced-apart relationship such that the bar of non-magnetic material is placed in the effective flux area of the permanent magnet, the magnetic devices being positioned in front of the apparatus such that each permanent magnet has its north pole opposed to the south pole of the other magnets and such that each bar of non-magnetic material is situated behind the permanent magnet associated thereto.

13 Claims, 1 Drawing Sheet

DEVICE TO REDUCE THE HAZARDS OF SURROUNDING ELECTROMAGNETIC RADIATION

This application is a continuation-in-part of patent application Ser. No. 07/725,042, filed Jul. 3, 1991, which was a continuation-in-part of patent application Ser. No. 07/070,946, filed Jul. 8, 1987, abandoned.

FIELD OF THE INVENTION

The invention relates in generally to the protection against the electromagnetic radiation emitted locally by an electric or electronic machine or apparatus and in particular to a device to remedy or prevent the radiation hazards from a locally generated electromagnetic field on an attendant or operator of an electric machine or apparatus.

BACKGROUND OF THE INVENTION

Electric and electronic machinery in general are known to emit electromagnetic radiation of various wavelengths. However, in the last few years the realization has gradually dawned that the habitual users of certain electronic machines and apparatus including the appliances and electronic devices that are becoming more and more common in offices or daily home life, are subject to physiological disorders. This is the case of the users of VDUs and television receivers. Since the introduction of such apparatus there have been many worker complaints which cannot be denied. The statistics collected in a number of countries have revealed in particular that the regular operators of such electronic machines suffer systematically from such complaints as eye-strain, dizziness, muscle ache, stiffneck, headache and irritability.

Although the exact causes of these complaints are still not completely understood and explained, various specialists who have observed and analyzed these phenomena attribute them chiefly to the electromagnetic radiation emitted by the machines.

In response to alarming reports on health concerns associated with VDU use, many international organisations, professional associations, research institutes or trade unions in several countries have developed model codes of practice or recommended guide-lines intended for personnel responsible for the selection and installation of VDUs and for workers who will use VDUs. Some guide-lines and model codes have included check-lists to assist in identifying problems and preventive or remedial measures.

Manufacturers have responded to said health concern by shielding their products against radiation leakage and introducing tiltable models with anti-glare features. Electromagnetic energy shielding currently uses energy absorbing material. For example, U.S. Pat. No. 4,218,507 discloses an energy absorbing composition comprising particles made of a metal core with an electrically conductive coating. Carbon compositions have also been used in radiation shielding applications.

State-of-the-art radiation shielding is effective to reduce or limit radiation leakage from electronic machines, and it has been reported that commonly no measurable level of radiation was detected. However, there are still many complaints from VDU users and the question of preventing radiation hazards is still debated in many countries. It has been recognized that an indication that no measurable level of radiation could be detected heretofore does not give any evidence that there is no radiation hazards any more. In the United States, for instance, NYCOSH (New York Committee for Occupational Safety and Health, Inc.) stated that "the testing which has been done is limited and has been challenged. Some radiation frequencies have not been tested for and most machines have not been tested at all. Manufacturing defects or poor maintenance could cause higher levels of radiation to be emitted. In addition, very low doses of radiation can be hazardous and there is no known safe level of exposure.

In Canada too, the question is at issue. In recommendations dated 1982, the Labour Canada Task Force on Micro-Electronics and Employment stated that "little is known about potential long-term effects of exposure to low-level radiation, . . . " and further that "the Task Force recommends that the canadian and provincial governments continue to fund medical and other research into possible safety and health risks, including the adequacy of currently acceptable radiation levels . . . ".

In many other countries, e.g. Japan and United Kingdom, it has been recognized that no definite conclusion has been reached as yet regarding the possible causal effect of long-term low-level radiation emission from VDUs. Reference can be made to the publication "Conditions of Work Digest", by the International Labour Office, Geneva, Volume 5, Number 1, 1986.

The applicant has studied this problem and, based on the idea that living cells grow and develop naturally when they are in a spectrally balanced magnetic field, believes that the foregoing complaints and disorders result from a spectral imbalance in the surrounding electromagnetic field due to an excess of harmful radiation generated by electronic machines.

SUMMARY OF THE INVENTION

It is therefore an object of the present invention to provide a technique and device whereby the radiation surrounding in front of an electric appliance or apparatus can be substantially altered so as to substantially prevent the harmful electromagnetic radiation emanating from the electric appliance or apparatus to reach the operator of the apparatus.

Another object of the invention is to provide a technique and device which are readily adaptable to existing electric apparatus and appliance without needing any structural modification of the apparatus or appliance.

A further object of this invention is providing a magnetic device that is easy to manufacture and to use in embodying the invention.

Briefly stated, the invention uses particular magnetic devices arranged in such a way as to create a substantially strong magnetic barrier in front of an electric apparatus or appliance emitting electromagnetic radiation.

The arrangement and device according to the invention and the method of carrying out the invention are defined in the appended claims.

The objects, advantages and features of the present invention will be best understood by reference to the following drawing and description.

DESCRIPTION OF AN EXEMPLARY EMBODIMENT

Figure 1:
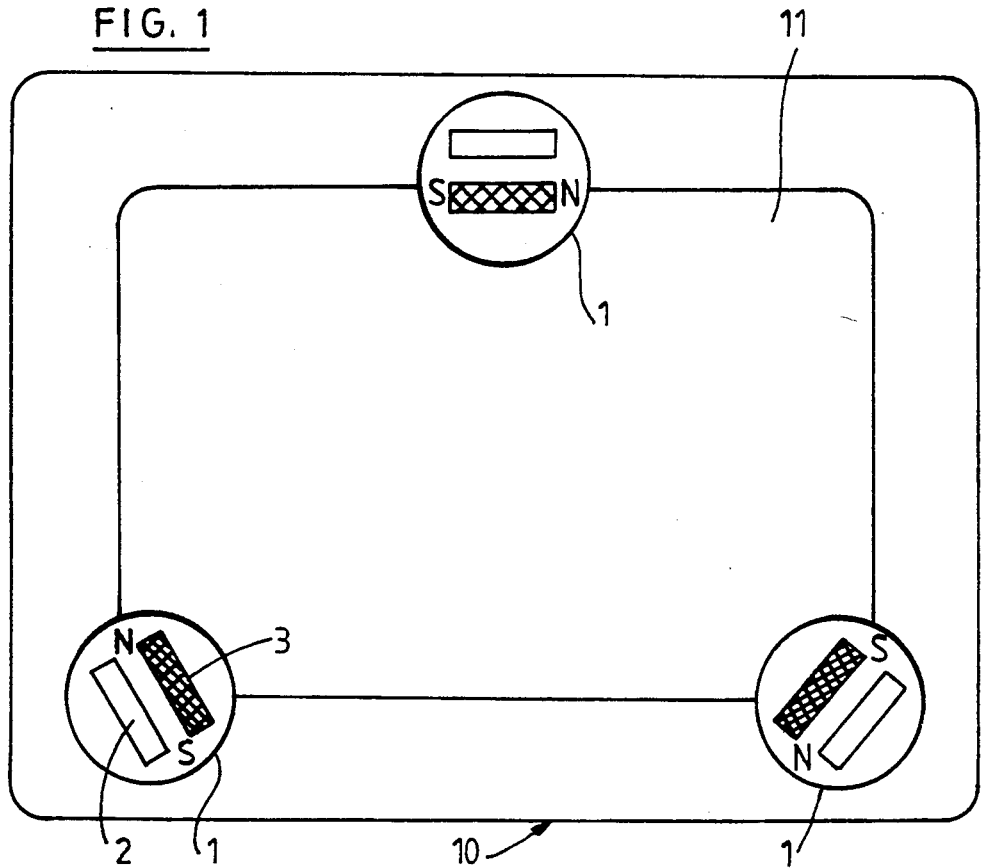
FIG. 1 shows a typical VDU with three devices embodying the invention arranged on the front face of the VDU.
Figure 2:
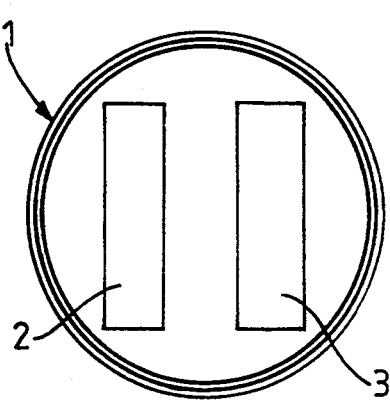
FIG. 2 is a top view of one of the devices shown in FIG. 1, with the cover removed.

In FIG. 1 there is shown the front face of a VDU 10 with its cathode-ray screen 11. The basic idea of this invention is to modify the radiation surrounding in front of unit 10 with the purpose of reducing the hazards of harmful electromagnetic radiation on the user of the unit 10. In order to obtain the desired alteration of the surrounding, the invention provides an arrangement for creating a substantially strong magnetic barrier in front of apparatus 10.

In embodying the invention use is made of a plurality of magnetic devices 1 arranged on the front face of the apparatus 10 so as to define an area in front of a major portion of the surface of the screen 11. At least three magnetic devices are to be used. FIG. 1 shows three magnetic units 1 approximately located at the apices of a triangle on the front face of the apparatus.

Figure 3:
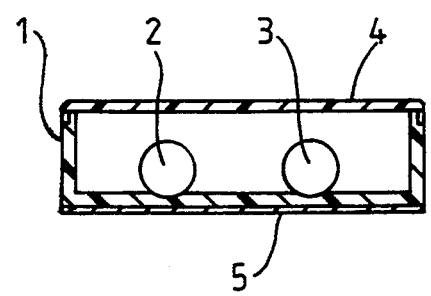
FIG. 3 is a cross-sectional view of the device of FIG. 2.

Each magnetic device 1 includes a non-metallic closed receptacle 1, for example a polystyrene box having a diameter of about 60 mm. Within the box are located a permanent magnet 2 for producing a magnetic flux and a bar 3 made of a non-magnetic material. These parts have for example a length of 20 mm and are adapted in recesses provided in the bottom of the box 1. As shown in FIG. 3 the cover 4 sealingly fits the upper edge of the box. The two parts 2 and 3 are in spaced apart relationship such that the non-magnetic bar 3 is traversed by magnetic flux lines produced by the magnet. The parts can also be embedded in a resin compound.

As an example, the permanent magnet 2 is made of a compound sold on the market under the name of Alcomax III with the following approximate composition by weight: 8.1% aluminium, 13.5% nickel, 24% cobalt, 2.5% copper, 0.5% niobium and 51.4% iron. The magnet should have a substantially high magnetization to be chosen in the range from 500 to 3300 Gauss or so. The bar 3 of non-magnetic material consists for instance of Ellor 9 graphite, a fine-grained isotropic pure graphite yielding a maximum of 0.1% ash on combustion and with a density of approximately 1.80 g/cm3 and a resistivity of approximately 1500 u$\Omega$cm. Bar 3 may also be composed essentially of magnesium.

The bottom of box 1 is provided with attachment means, e.g. a self adhesive means 5 for allowing the device to be attached to a machine or appliance. The magnetic devices 1 are positioned on the front face of the apparatus 10 such that each magnet 2 has its north pole N opposed to the south pole S of the other magnets and such that each bar 3 of non-magnetic material is situated behind the magnet associated thereto.

The bars 3 of non-magnetic material act as shielding elements behind the magnets 2 and as a sink for the electromagnetic radiation. The strong magnetic flux produced by the permanent magnets is thereby mostly located in the area surrounded by the magnets 2 in front of the screen 11, thus resulting in a strong magnetic barrier or gate to be created there.

Tests were carried out using magnetic devices as described in the foregoing comprising strongly magnetized permanent magnets and bars composed essentially of carbon or graphite. These tests have shown that, by virtue of the present invention, the operators of electronic machines with cathode-ray screens could use the machines regularly and intensively without the recurrence of the complaints and disorders that usually follow after working on such machines.

Without giving a scientific explanation of the phenomenon that he has observed, the applicant hypothesizes that in use, the strong magnetic barrier created in accordance with this invention in front of the apparatus is effective to impede the passage of harmful electromagnetic radiation from the apparatus to the operator of the apparatus. The operator is thereby kept safe from at least a substantial portion of harmful electromagnetic radiation emanating from the apparatus with the result that he is less subject to the usual radiation hazards.

It is recognized indeed that magnetic flux produced by permanent magnets does not cause any physiological disorder. The advantages of the invention can be obtained readily when using any existing electric apparatus by simply positioning at least three magnetic devices according to the invention on the front face of the apparatus in the way outlined herein above.

Using the invention is not limited to machines with cathode-ray screens, but includes household appliances (microwave ovens, for example), computers, motor vehicles, and so on. When the machine is relatively large, it is suitable to arrange more than three units distributed over its entire front surface.

Although there has been described herein before a particular embodiment in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the appended claims.

I claim:

1. In combination with an electric apparatus emitting electromagnetic radiation, an arrangement for reducing the radiation hazards on an operator in front of the apparatus, said arrangement comprising at least three magnetic devices approximately located at the apices of a triangle in front of the apparatus, each magnetic device including a closed housing made of a non-magnetic material, a permanent magnet located within said housing for producing a magnetic flux, and a bar of non-magnetic material located within said housing in a defined spaced-apart relationship such that said bar of non-magnetic material is placed in the effective flux area of the permanent magnet, said magnetic devices being positioned in front of the apparatus such that each permanent magnet has its north pole opposed to the south pole of the other magnets and such that each bar of non-magnetic material is situated behind the permanent magnet associated thereto.

2. The device of claim 1, wherein the permanent magnet is made of a compound having the following approximate composition by weight: 8.1% aluminium, 13.5% nickel, 24% cobalt, 2.5% copper, 0.5% niobium, and 51.4% iron.

3. The device of claim 1, wherein said bar of non-magnetic material is composed essentially of fine-grained isotropic pure graphite.

4. The device of claim 3, wherein the pure graphite bar is composed of an isotropic graphite yielding no more than approximately 0.1% ash upon combustion and with a density of approximately 1.80 g/cm3 and a resistivity of approximately 1500 μΩcm.

5. The device of claim 1, wherein the housing has attachment means for the attachment of the device onto an apparatus.

6. The device of claim 1, wherein said bar of non-magnetic material is composed essentially of magnesium.

7. A method for reducing the radiation hazards in front of an electronic apparatus emitting electromagnetic radiation, the method comprising the steps of using at least three magnetic devices to create a local magnetic barrier in front of the apparatus by placing said at least three magnetic devices approximately at the apices of a triangle on the front face of said apparatus, each magnetic device including a closed housing made of a non-metallic material, a permanent magnet for producing a magnetic flux, a bar of non-magnetic material located within the housing, and means for positioning the permanent magnet and the bar of non-magnetic material in a defined spaced-apart relationship such that said bar of non-magnetic material is placed in the effective flux area of the permanent magnet, and positioning said magnetic devices in front of the apparatus such that each permanent magnet has its north pole opposed to the south pole of the other magnets and such that each bar of non-magnetic material is situated behind the permanent magnet associated thereto.

8. A device for use in combination with an electric apparatus emitting electromagnetic radiation to reduce the surrounding electromagnetic radiation in front of the electric apparatus, including
   a closed housing made of a non-metallic material,
   a permanent magnet located within said housing for producing a magnetic flux, said permanent magnet being made of a compound having the following approximate composition by weight: 8.1% aluminum, 13.5% nickel, 24% cobalt, 2.5% copper, 0.5% niobium and 51.4% iron,
   a bar of non-magnetic material located within said housing, and
   means for positioning the permanent magnet and the bar of non-magnetic material in a defined spaced-apart relationship such that said bar of non-magnetic material is placed in the effective flux area of the permanent magnet.

9. The device of claim 8, wherein said means for positioning the permanent magnet and said bar of non-magnetic material includes an embedding resin compound.

10. A device for use in combination with an electric apparatus emitting electromagnetic radiation to reduce the surrounding electromagnetic radiation in front of the electric apparatus, comprising:
    a closed housing made of a non-metallic material,
    a permanent magnet located within said housing for producing a magnetic flux,
    a bar of fine-grained isotropic pure graphite located within said housing, and
    means for positioning the permanent magnet and the bar of graphite in a defined spaced-apart relationship such that said bar of graphite is placed in the effective flux area of the permanent magnet.

11. The device of claim 10, wherein said means for positioning the permanent magnet and said bar of non-magnetic material includes an embedding resin compound.

12. A device for use in combination with an electric apparatus emitting electromagnetic radiation to reduce the surrounding electromagnetic radiation in front of the electric apparatus, including
    a closed housing made of a non-metallic material,
    a permanent magnet located within said housing for producing a magnetic flux,
    a bar of isotropic graphite located within said housing, said bar of isotropic graphite yielding no more than approximately 0.1% ash upon combustion and with a density of approximately 1.80 g/cm$^3$ and a resistivity of approximately 1500 μΩcm, and
    means for positioning the permanent magnet and the bar of non-magnetic material in a defined spaced-apart relationship such that said bar of non-magnetic material is placed in the effective flux area of the permanent magnet.

13. The device of claim 12, wherein said means for positioning the permanent magnet and said bar of non-magnetic material includes an embedding resin compound.

* * * * *